(12) United States Patent
Vaughn et al.

(10) Patent No.: US 11,426,253 B2
(45) Date of Patent: Aug. 30, 2022

(54) SYSTEM FOR PROVIDING HANDS-FREE ILLUMINATION

(71) Applicants: Tanya M. Vaughn, Stillwater, OK (US); Larry J. Vaughn, Stillwater, OK (US)

(72) Inventors: Tanya M. Vaughn, Stillwater, OK (US); Larry J. Vaughn, Stillwater, OK (US)

( * ) Notice: Subject to any disclaimer, the term of this patent is extended or adjusted under 35 U.S.C. 154(b) by 441 days.

(21) Appl. No.: 16/708,650

(22) Filed: Dec. 10, 2019

(65) Prior Publication Data

US 2020/0113644 A1     Apr. 16, 2020

Related U.S. Application Data

(63) Continuation of application No. 15/838,004, filed on Dec. 11, 2017, now Pat. No. 10,512,521.

(Continued)

(51) Int. Cl.

| | |
|---|---|
| *A61B 1/06* | (2006.01) |
| *A61B 90/35* | (2016.01) |
| *A61M 25/01* | (2006.01) |
| *F21V 23/04* | (2006.01) |
| *A61B 50/33* | (2016.01) |

(Continued)

(52) U.S. Cl.
CPC .............. *A61B 90/35* (2016.02); *A61B 5/259* (2021.01); *A61B 50/33* (2016.02); *A61M 25/01* (2013.01); *F21V 23/04* (2013.01); *A61B 50/20* (2016.02); *A61B 2017/00424* (2013.01); *A61B 2050/314* (2016.02); *A61B 2090/309* (2016.02); *A61M 2205/587* (2013.01); *F21V 21/0808* (2013.01); *F21V 21/30* (2013.01); *F21W 2131/205* (2013.01); *F21Y 2115/10* (2016.08)

(58) Field of Classification Search
CPC combination set(s) only.
See application file for complete search history.

(56) References Cited

U.S. PATENT DOCUMENTS

| | | |
|---|---|---|
| 4,233,987 A | 11/1980 | Feingold |
| 4,583,549 A | 4/1986 | Manoli |

(Continued)

OTHER PUBLICATIONS

"Titanium Innovations Keylight Keychain LED Light—Various Colors" website; retrieved from https://www.batteryjunction.com/titanium-keylight.html: last visited Dec. 11, 2018.

(Continued)

*Primary Examiner* — Sameh R Boles
(74) *Attorney, Agent, or Firm* — Dunlap Codding, P.C.

(57) ABSTRACT

Methods and systems are disclosed including a light system comprising a pad assembly comprising: a pad having a first side and a second side opposite the first side, the first side having an adhesive thereon; and a post with a proximal end connected to the second side of the pad and extending to a rounded distal end; and a light assembly attachable to and rotatable about the rounded distal end of the post of the pad assembly, the light assembly comprising: a case having an opening, the opening structured to rotatably accept the rounded distal end of the post of the pad assembly; one or more light emitting diode at least partially within the case and positioned to illuminate an area outside of the case.

20 Claims, 10 Drawing Sheets

Related U.S. Application Data

(60) Provisional application No. 62/454,287, filed on Feb. 3, 2017.

(51) Int. Cl.
*A61B 5/259* (2021.01)
*F21V 21/08* (2006.01)
*F21V 21/30* (2006.01)
*F21W 131/205* (2006.01)
*A61B 90/30* (2016.01)
*A61B 17/00* (2006.01)
*F21Y 115/10* (2016.01)
*A61B 50/20* (2016.01)
*A61B 50/30* (2016.01)

(56) References Cited

U.S. PATENT DOCUMENTS

| | | | |
|---|---|---|---|
| 6,039,454 | A | 3/2000 | Hallgrimsson |
| 9,243,739 | B2 | 1/2016 | Peters |
| 10,357,146 | B2 | 7/2019 | Fiebel et al. |
| 2005/0099824 | A1 | 5/2005 | Dowling et al. |
| 2016/0287814 | A1* | 10/2016 | McManus .............. A61B 90/30 |
| 2017/0065360 | A1 | 3/2017 | Nichols |

OTHER PUBLICATIONS

WIPO International Searching Authority, International Search Report and Written Opinion regarding PCT/US18/64930 dated Mar. 18, 2019.

\* cited by examiner

SYSTEM FOR PROVIDING HANDS-FREE ILLUMINATION

CROSS REFERENCE TO RELATED APPLICATIONS, INCORPORATION BY REFERENCE

The present patent application is a continuation of, and claims priority to, the patent application identified by U.S. Ser. No. 15/838,004, filed Dec. 11, 2017, titled "Method for Providing Hands-Free Illumination During Medical Procedures"; and claims priority to the provisional patent application identified by U.S. Ser. No. 62/454,287, filed Feb. 3, 2017; the entire contents of each of which are hereby expressly incorporated by reference herein.

FIELD OF THE DISCLOSURE

The disclosure generally relates to methods and systems that provide hands-free illumination on a desired area of a patient during medical procedures and care-giving procedures.

BACKGROUND

In the medical industry, it is important for medical personnel and caregivers to have illumination of the area of the patient that requires care. The personnel are often performing delicate and exacting work that requires that the personnel have a clear view of the area. For example, the personnel may be cleaning a wound and must be sure that all debris is removed. Or they may be inserting a catheter, an intravenous tube, a central line, stitches, and so on, all of which require a clear view of the area, preferably without shadow, interference in lighting, or gaps in lighting.

Overhead lights or offset lights to the side of the patient are often inadequate to illuminate the desired area for several reasons. For example, the caregiver is often leaning over the patient, which blocks the illumination from the overhead or offset lights from the area. Additionally, the patient's own body may cast shadows over the area.

Further, headlamps and finger lamps worn by the personnel or caregiver personnel may also be inadequate in that any movement of the personnel causes the illumination to shift or move away from the area of care. Also, when multiple medical personnel and/or caregiver personnel are working with a patient, a light worn by one of the personnel can inadvertently shine into the eyes of the other personnel, causing problems and distractions which may prove dangerous to the patient by causing error or inattention during important medical procedures. Therefore, systems and methods for hands-free illumination of a patient during medical and care-giving procedures are needed that addresses at least the described problems.

SUMMARY

A method and system for providing hands-free illumination during medical procedures and caregiving to a patient are disclosed. The problem of inadequate illumination for the affected area of a patient is addressed through a method of adhering a sterile light system to the patient and as described herein.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
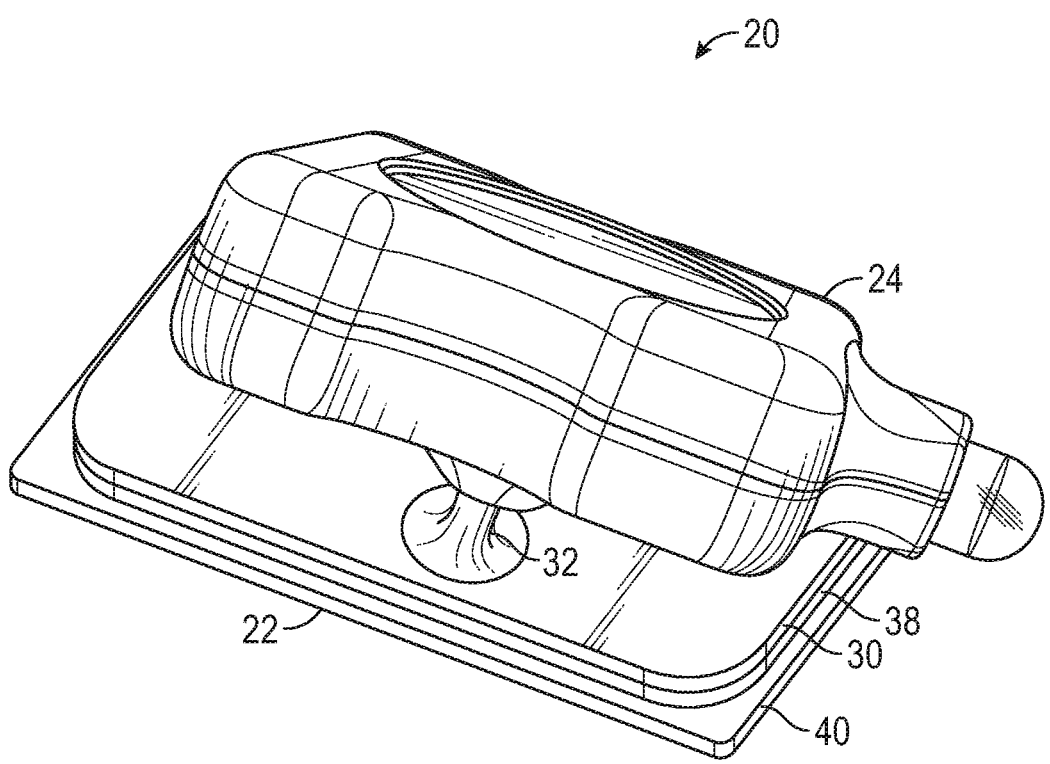
FIG. 1 is a perspective view of an exemplary sterile light system in accordance with the present disclosure.
Figure 2:
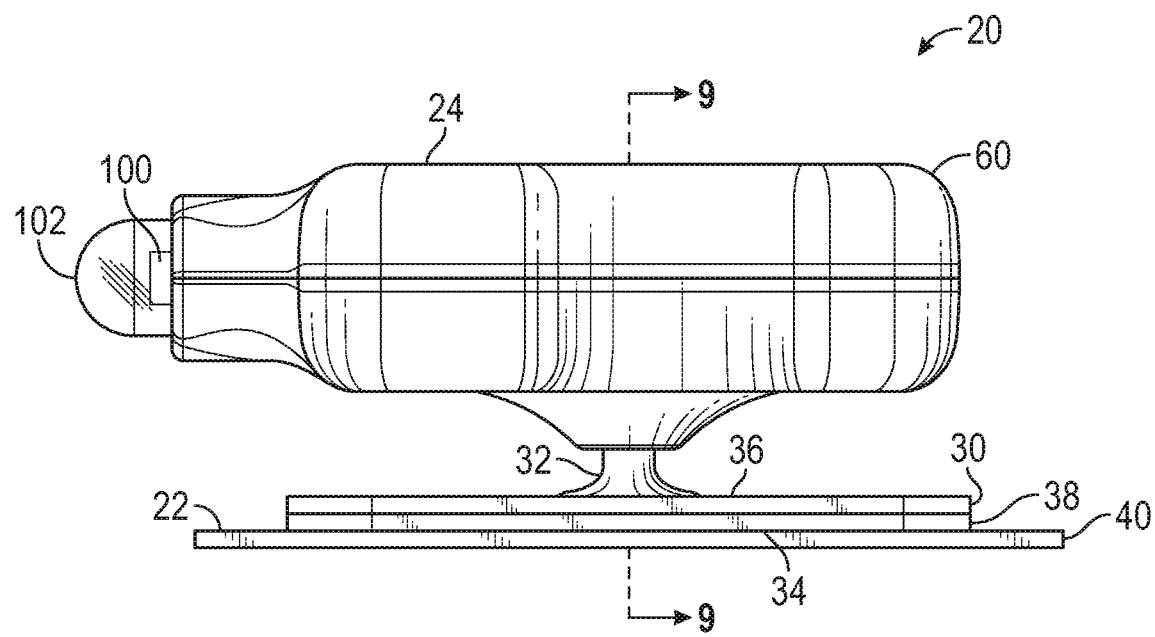
FIG. 2 is a first side elevational view of the exemplary sterile light system of FIG. 1.
Figure 3:
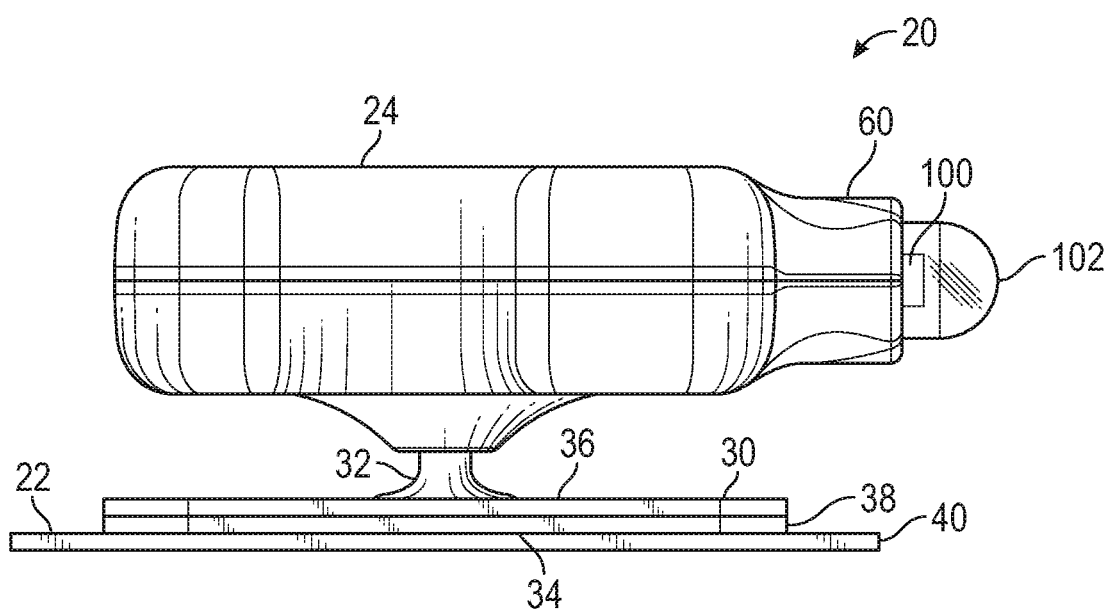
FIG. 3 is a second side elevational view of the exemplary sterile light system of FIG. 1.
Figure 4:
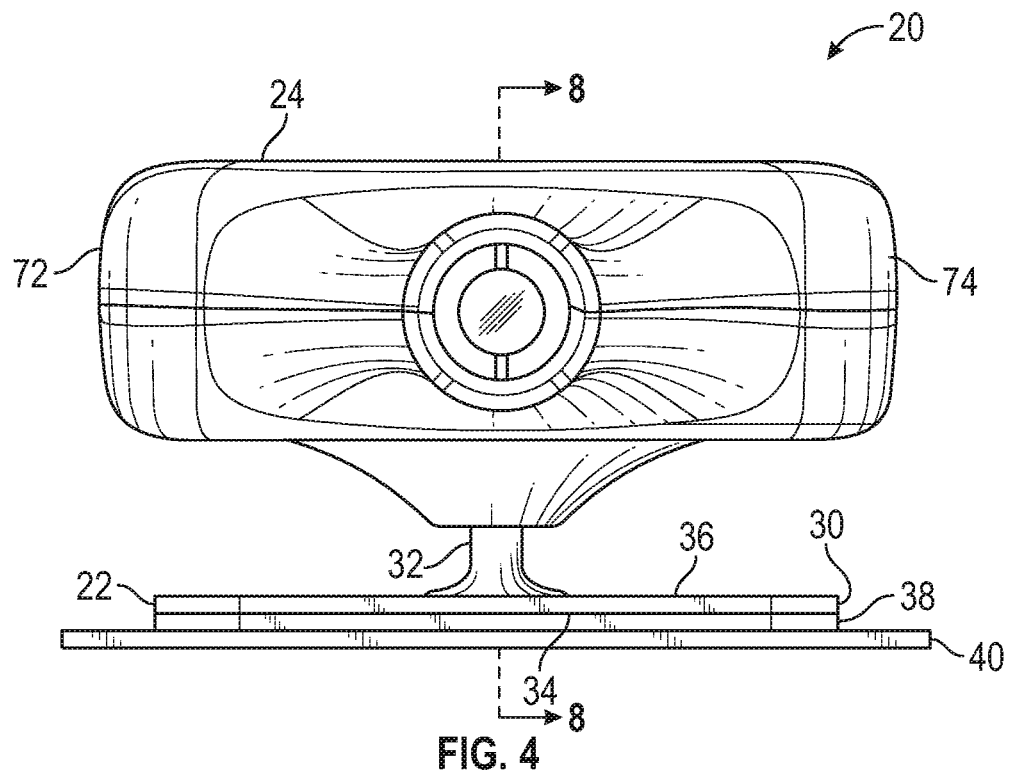
FIG. 4 is a front elevational view of the exemplary sterile light system of FIG. 1.
Figure 5:
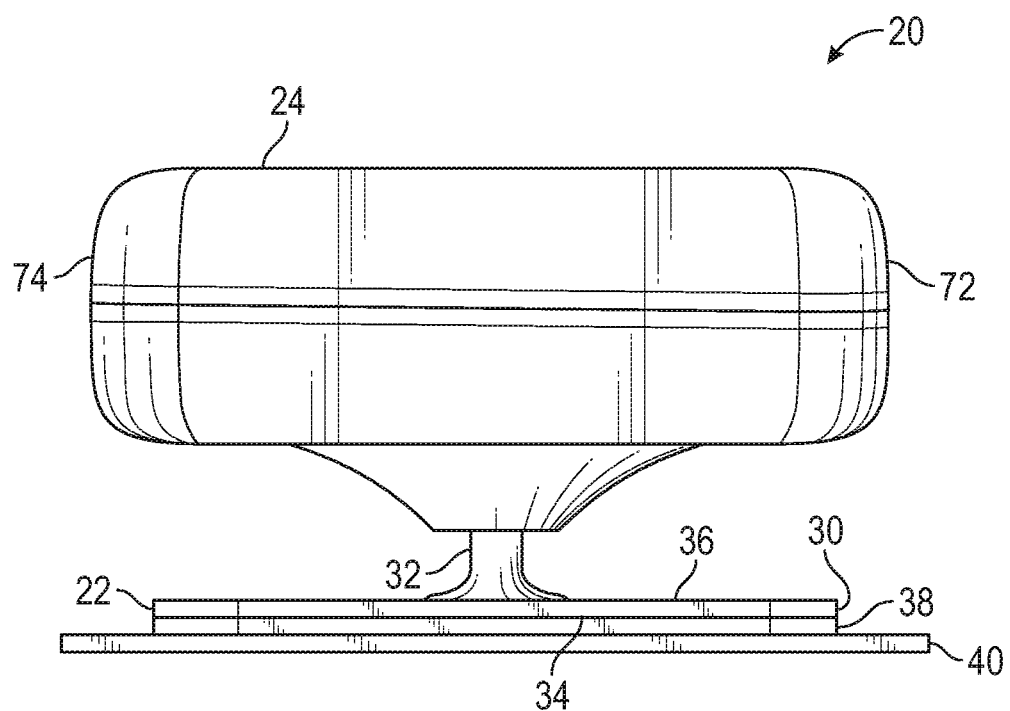
FIG. 5 is a back elevational view of the exemplary sterile light system of FIG. 1.

The following detailed description refers to the accompanying drawings. The same reference numbers in different drawings may identify the same or similar elements.

The mechanisms proposed in this disclosure circumvent the problems described above. The present disclosure describes systems and methods for hands-free illumination of an area on a patient during medical and/or care-giving procedures. In an exemplary embodiment a method for providing hands-free illumination during medical procedures, comprises obtaining a sterile light system. The sterile light system may comprise a sterile pad assembly and a sterile light assembly. The sterile pad assembly may comprise a pad having a first side and a second side opposite the first side, the first side having an adhesive thereon; a removable protective sheet covering the adhesive such that the adhesive is exposed when the protective sheet is removed; and a post with a proximal end connected to the second side of the pad and extending to a rounded distal end. The sterile light assembly may be attachable to and rotatable about the distal end of the post of the pad assembly. The sterile light assembly may comprise a case having an opening, the opening structured to rotatably accept the rounded distal end; one or more light emitting diode positioned to illuminate an area outside of the case; one or more power source connected to the light emitting diode; and one or more switch connected to the light emitting diode and the power source such that the switch controls a flow of power from the power source to the light emitting diode. The method may further comprise activating the switch to turn on the flow of power from the power source to the light emitting diode and illuminating the area of the patient for which illumination is desired with the light system. The method may further comprise performing a medical and/or care-giving procedure on/in the illuminated area of the patient.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As discussed above, current methods of illumination for procedures on a patient 42 are insufficient for many procedures that medical personnel and care-givers perform on a patient 42. The present disclosure addresses these deficiencies with a methodology for providing hands-free illumination for medical and care-giving procedures.

Referring now to the drawings, FIGS. 1-7 illustrate a sterile light system 20 in accordance with the present disclosure. The sterile light system 20 comprises a sterile pad assembly 22 and a sterile light assembly 24.

The term "sterile" refers to the result of the medically recognized process of decontamination. Sterilization is the physical or chemical process that renders an inanimate object, when may be contaminated with harmful microbial life, safe for handling and use. The objective of sterilization is to protect personnel and patients from contracting diseases and infections, such as those caused by microorganisms and pathogens. Sterilization reduces or eliminates microorganisms and pathogens on an object to produce a sterile object. Sterilization may be achieved through many recognized processes including, but not limited to, the use of one or more of chlorine dioxide gas, heat, steam, ethylene oxide gas, formaldehyde gas, microwaves, hydrogen peroxide plasma, ozone gas, chemical solutions, ionizing radiation, and so on.

As shown in FIGS. 1-5, 7-9, and 11, the sterile pad assembly 22 comprises a pad 30 and at least one post 32. The pad 30 has a first side 34 and a second side 36 opposite the first side. In one embodiment, the first side 34 has an adhesive 38 on the first side. In one embodiment, the sterile pad assembly 22 further comprises a removable protective sheet 40 covering the adhesive 38 such that the adhesive 38 is exposed when the protective sheet 40 is removed.

The adhesive 38 may be an adhesive that is capable of adhering and holding the pad assembly 22 and the light assembly 24 of the sterile light system 20 to the skin of a patient 42 and of being removed from the skin of the patient 42 by pulling the sterile pad assembly 22 away from the skin of the patient 42. In one embodiment, the adhesive 38 may be formulated such that a force used to pull the sterile pad assembly 22 away from the skin of the patient 42 may be minimal, in that the patient 42 is not caused discomfort when the sterile pad assembly 22 is removed.

In one embodiment, the adhesive 38 may be water-soluble and/or chemically soluble such that the adhesive 38 dissolves in the presence of water and/or chemical solutions, thereby losing its adhesive qualities. In one embodiment, the adhesive 38 may be water resistant.

In one embodiment, the adhesive 38 may be an acrylate-based adhesive. In one embodiment, the adhesive 38 may be a gel adhesive. In one embodiment, the adhesive 38 may be a silicone-based adhesive and/or a polyurethane-based adhesive. In one embodiment, the adhesive 38 may comprise two or more layers of adhesive materials. In one embodiment, the adhesive 38 may be a cured substrate coating. It will be understood by those having ordinary skill in the art that other suitable adhesives may be used that stick to human skin and that may be easily removed from human skin with minimal pain to the patient 42.

In one embodiment, the adhesive 38 may be formulated of hypoallergenic materials. The adhesive 38 may contain only minimal amounts of residual monomers due to a high degree of polymerization and may thus be well tolerated by the skin.

In one embodiment, the post 32 has a proximal end 50 connected to the pad 30 and extending to a rounded distal end 52. In one embodiment, the proximal end 50 is connected to the second side 36 of the pad 30. In one embodiment, the proximal end 50 is secured within the pad 30.

In one embodiment, the rounded distal end 52 is shaped as a snap having a circular lip. In one embodiment, the rounded distal end 52 is spherical.

In one embodiment, the post 32 has a center portion 54 and the rounded distal end 52 of the post 32 has a larger diameter than the width and/or diameter of the center portion 54 of the post 32.

In one embodiment, the pad assembly 22 is an electrocardiography pad and electrode. In one embodiment, the pad assembly 22 is a pediatric electrocardiography pad and electrode. In one embodiment, the pad assembly 22 is comprised of hypoallergenic materials.

Figure 6:
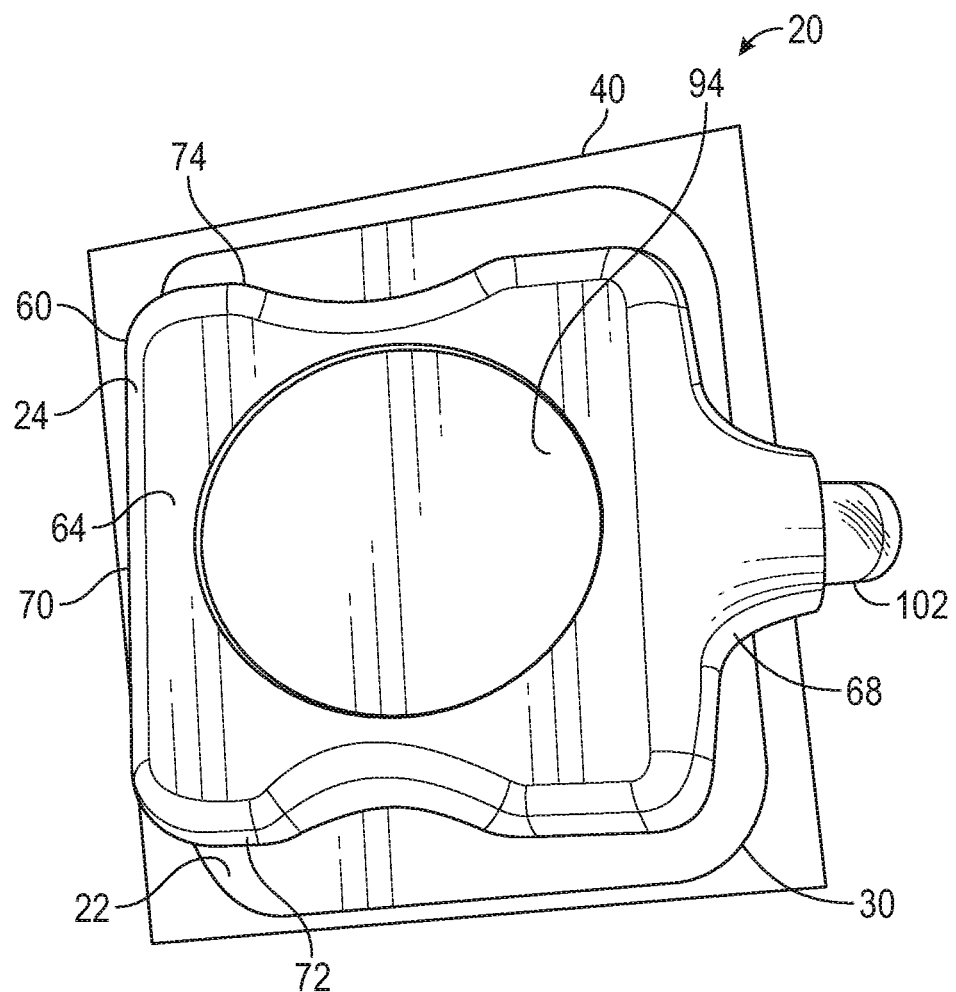
FIG. 6 is a top plan view of the exemplary sterile light system of FIG. 1.
Figure 7:
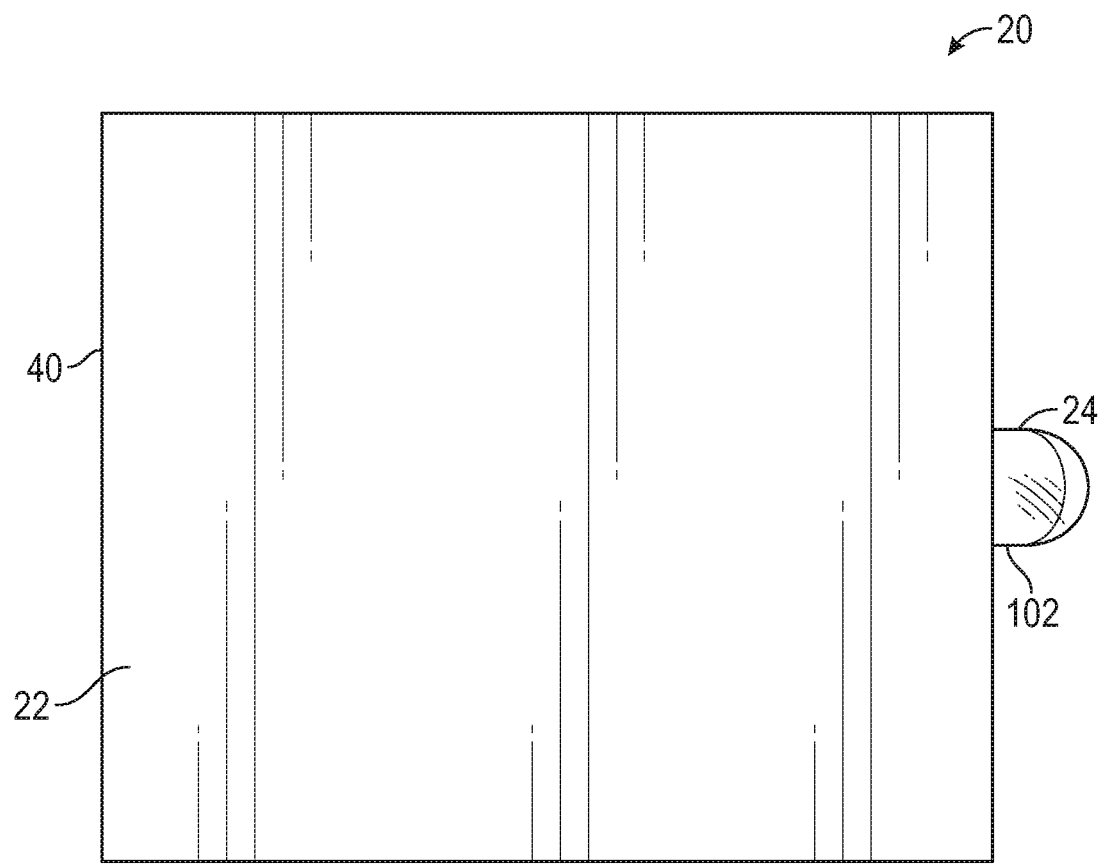
FIG. 7 is a bottom plan view of the exemplary sterile light system of FIG. 1.

Referring now to FIGS. 1 and 6, the sterile light assembly 24 is attachable to, and rotatable about, the distal end 52 of the post 32 of the pad assembly 22. The sterile light assembly 24 may be rotatable three-hundred and sixty degrees about a central axis of the post 32 approximately perpendicular to the pad 30. The sterile light assembly 24 may be rotatable about the distal end 52 of the post 32 about an axis parallel to the pad 30. The sterile light assembly 24 may be adjustable in pitch, yaw, and roll in relation to the post 32 and/or the pad 30. In one embodiment, the sterile light assembly 24 may stay in the position to which it is adjusted until the sterile light assembly 24 is adjusted to a new position in pitch, yaw, and roll in relation to the post 32 and/or the pad 30. For purposes of illustration, the light assembly 24 shown in FIGS. 1 and 6 is shown in a partially rolled position. For clarity, other figures may not depict the rolled position.

Figure 8:
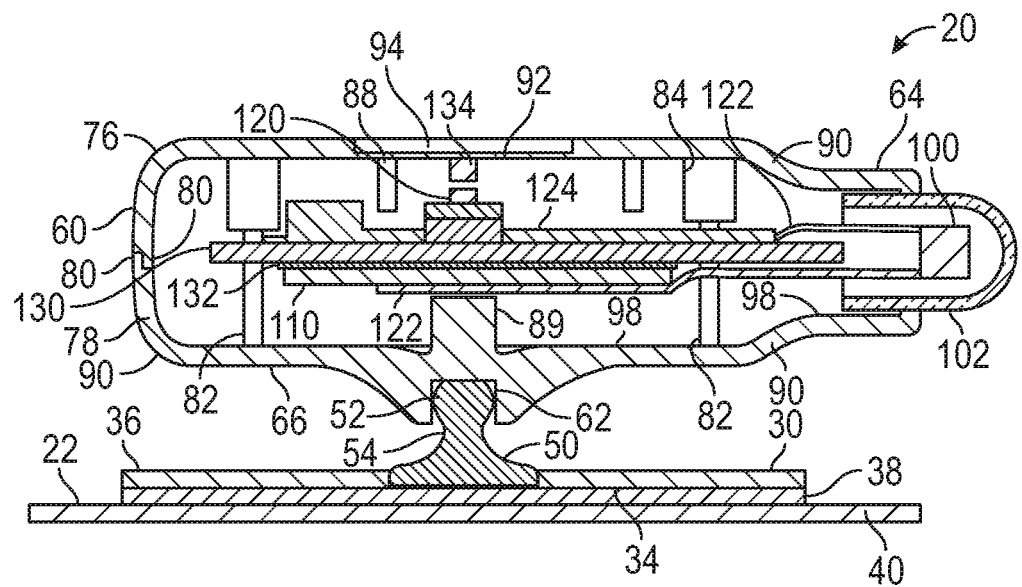
FIG. 8 is a cross-sectional view of the exemplary sterile light system taken along line 8-8 of FIG. 4.
Figure 9:
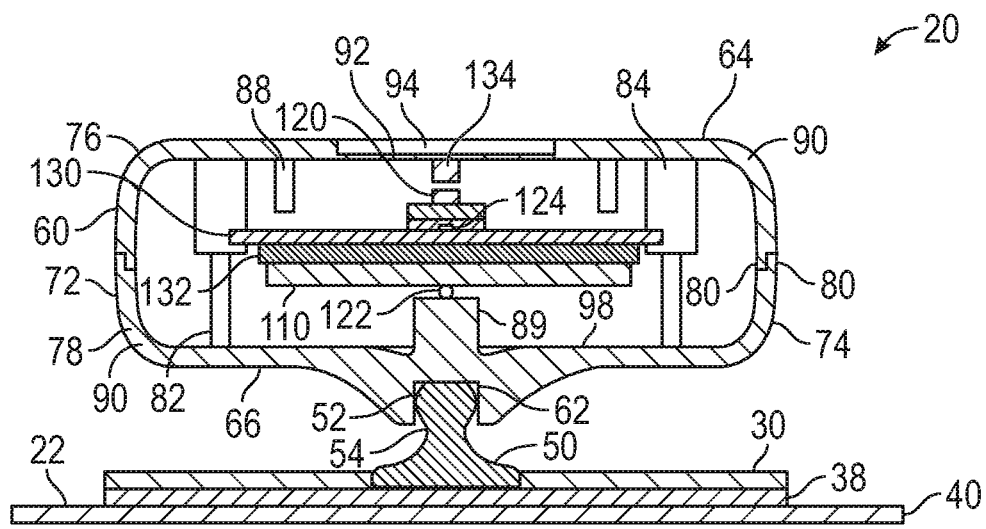
FIG. 9 is a cross-sectional view of the exemplary sterile light system taken along line 9-9 of FIG. 2.
Figure 10:
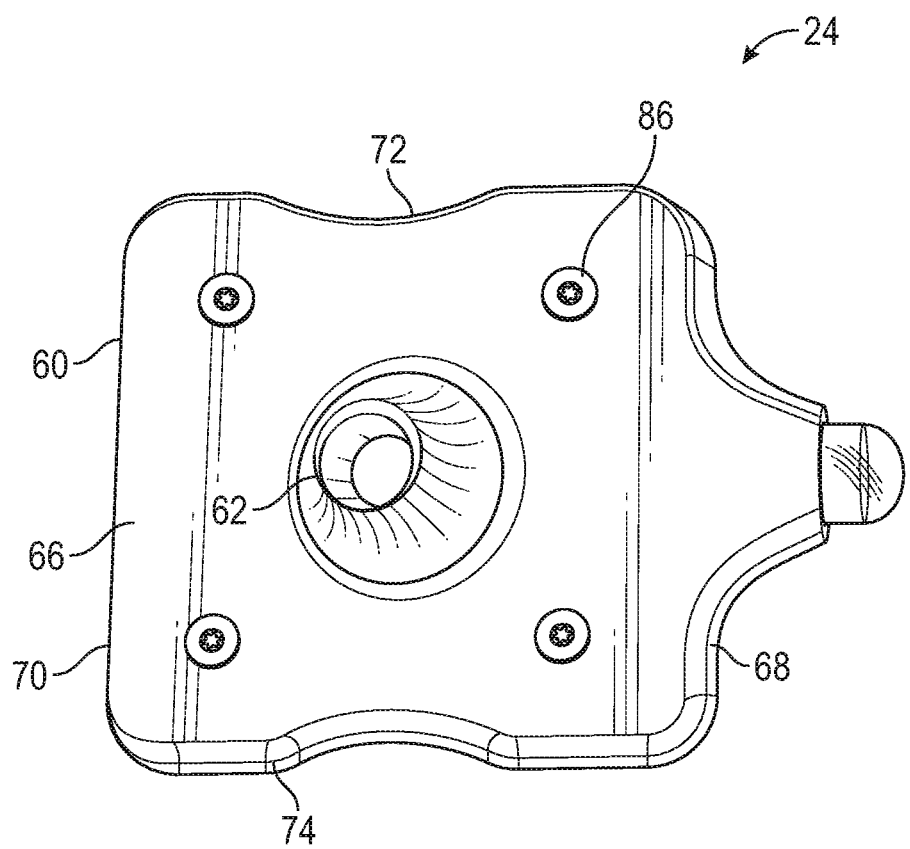
FIG. 10 is a bottom plan view of an exemplary sterile light assembly in accordance with the present disclosure.
Figure 11:
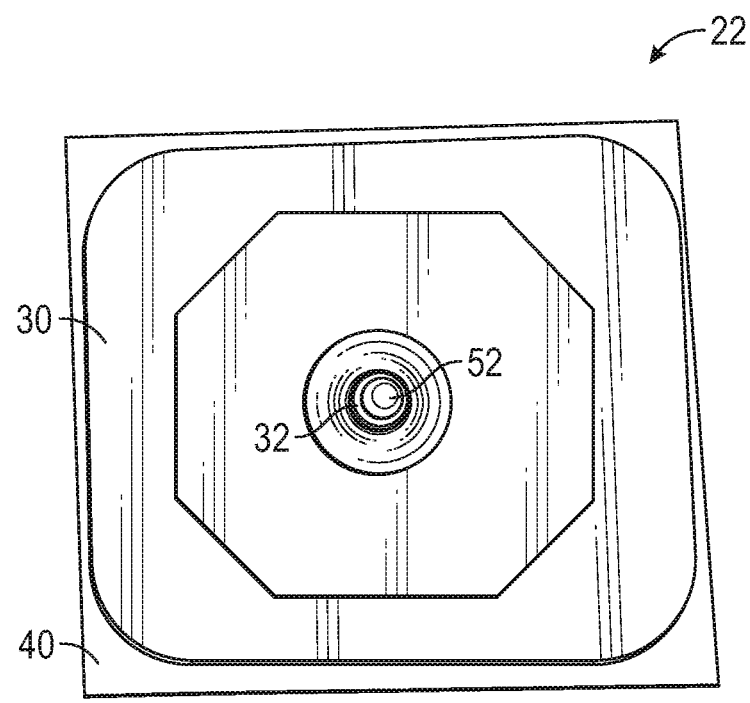
FIG. 11 is a top plan view of an exemplary pad assembly in accordance with the present disclosure.

As shown in FIGS. 8-10, in one embodiment, the sterile light assembly 24 may comprise a case 60 having an opening 62. The opening 62 may be structured to rotatably accept the rounded distal end 52 of the post 32. In one embodiment, at least a portion of the opening 62 may be smaller than the rounded distal end 52 of the post 32 such that the rounded distal end 52 of the post 32 is press-fit into the opening 62 when the light assembly 24 is attached to the post 32.

In one embodiment, the case further has a top 64, a bottom 66, a front 68, a back 70, a first side 72 extending from the front 68 to the back 70 between the top 64 and the bottom 66, and a second side 74 opposite the first side 72 and extending from the front 68 to the back 70 between the top 64 and the bottom 66. In one embodiment, the opening 62 that is structured to rotatably accept the rounded distal end 52 of the post 32 is located on the bottom 66 of the case 60.

As shown in FIGS. 8, 9, and 12-15, in one embodiment, the case 60 of the light assembly 24 comprises a top portion 76 attached to a bottom portion 78. In one embodiment, the top portion 76 and/or the bottom portion 78 may have one or more lips 80 that fits into the opposite portion 76, 78. In one embodiment, the top portion 76 and the bottom portion 78 are press fit together. In one embodiment, one of the top portion 76 and the bottom portion 78 has one or more pins 82 and the other of the top portion 76 and the bottom portion 78 receives the pins 82, such as in one or more hollow cylindrical protrusions 84, or holes (not shown).

In one embodiment, as shown in FIG. 10, the top portion 76 and the bottom portion 78 are attached to one another with one or more fasteners 86. In one embodiment, the one or more fasteners 86 extend through the hollow cylindrical protrusions 84.

In one embodiment, one or more of the first side 72, the second side 74, the front 68, the back 70, the top 64, and the bottom 66 of the case 60 is at least partially curved. In one embodiment, the case 60 may be curved in an ornamental manner.

In one embodiment, one or more of the first side 72, the second side 74, the front 68, the back 70, the top 64, and the bottom 66 of the case 60 is ergonomically shaped to accept fingers of a user of the sterile light system 20. The term "ergonomically shaped" may be defined to include indentions, rounded indentions, ridges, texturing, or other shapes that assist the user in grasping, manipulating, activating, deactivating, and otherwise interacting with the sterile light system 20 in use, in a manner that increases the ease of use of the sterile light system 20 and decreases any risk of harm to the user.

In one embodiment, the case 60 has one or more exterior walls 90 having a first thickness. The exterior walls 90 of the case 60 may form and/or encompass an interior cavity 98 of the case 60. In one embodiment, one or both of the top portion 76 and the bottom portion 78 have one or more stops 88. The stops 88 may protrude from the interior of the top portion 76 and/or the bottom portion 78 into the interior cavity 98. In one embodiment, one or both of the top portion 76 and the bottom portion 78 have one or more supports 89. The supports 89 may protrude from the interior of the top portion 76 and/or the bottom portion 78 into the interior cavity 98.

In one embodiment, the case 60 is roughly rectangular. In one embodiment, the first side 72 and the second side 74 of the case 60 are approximately one and one-quarter inch long. In one embodiment, the front 68 and the back 70 of the case 60 are approximately one and one-eighth inch long. In one embodiment, the distance between the top 64 and the bottom 66 of the case 60 is approximately three-eighths of an inch. Of course, it will be understood that the case 60 may be other dimensions and/or shapes that are convenient for use on the patient 42.

In one embodiment, the one or more exterior walls 90 of the case 60 may have one or more thinned portion 92 that has a second thickness less than the first thickness of the exterior walls 90. In one embodiment, the one or more thinned portion 92 of the walls 90 is located in one or more of the first side 72, the second side 74, the front 68, the back 70, the top 64, and the bottom 66 of the case 60. In one embodiment, the one or more thinned portion 92 in the one or more walls 90 is indented in comparison to the surrounding area of the exterior of the case 60.

In one embodiment, one or more of the first side 72, the second side 74, the front 68, the back 70, the top 64, and the bottom 66 of the case 60, has one or more depression 94 and/or a raised portion 96 (not shown). In one embodiment, the one or more thinned portion 92 is located in the one or more depression 94 and/or raised portion 96.

In one embodiment, the light assembly 24 snaps onto the pad assembly 22. In one embodiment, the opening 62 of the case 60 and the distal end 52 of the post 32 of the pad assembly 22 create a snap fit when connected. In one embodiment, at least a portion of the case 60 around the opening 62 is at least partially elastically deformed, to exert an elastic retaining force on the distal end 62 of the post 32. In one embodiment, at least a portion of the case 60 around the opening 62 is at least partially permanently deformed, to exert a retaining force on the distal end 52 of the post 32. In one embodiment, elastic and/or permanent deformation of the portion of the case 62 around the opening retains the light assembly 24 in a rotated position (such as an adjustment in pitch, yaw, and/or roll of the light assembly 24).

In one embodiment, the opening 62 may be a blind-end hole into one of the walls 90 or other solid portion of the case 60. In one embodiment, the opening 62 may be a through-hole through one of the walls 90 of the case 60 leading into the interior cavity 98 of the case 60. In one embodiment, the opening 62 may have a lip (not shown).

In one embodiment, the rounded distal end 52 of the post 32 has a first diameter, and the opening 62 of the case 60 is rounded and has a second diameter smaller than the first diameter of the rounded distal end 52 of the post 32. In one embodiment, attaching the light assembly 24 to the distal end 52 of the post 32 of the pad assembly 22 creates a press fit between at least a portion of the opening 62 and the post 32.

Referring now to FIGS. 2-4 and 8, the sterile light assembly 24 further comprises one or more light emitting diode 100 located at least partially within the case 60 and positioned to illuminate an area outside of the case 60. In one embodiment, the one or more light emitting diode 100 may be located fully inside the case 60. In one embodiment, the light emitting diode 100 is proximate to the front 68 of the case 60. In one embodiment, the light emitting diode 100 extends at least partially out of the case 60. In one embodiment, the light emitting diode 100 is at least partially encompassed by a transparent or translucent cover 102.

In one embodiment, the one or more light emitting diode 100 produces light in the white color spectrum. In one embodiment, the one or more light emitting diode 100 produces light in any color spectrum.

Figure 12:
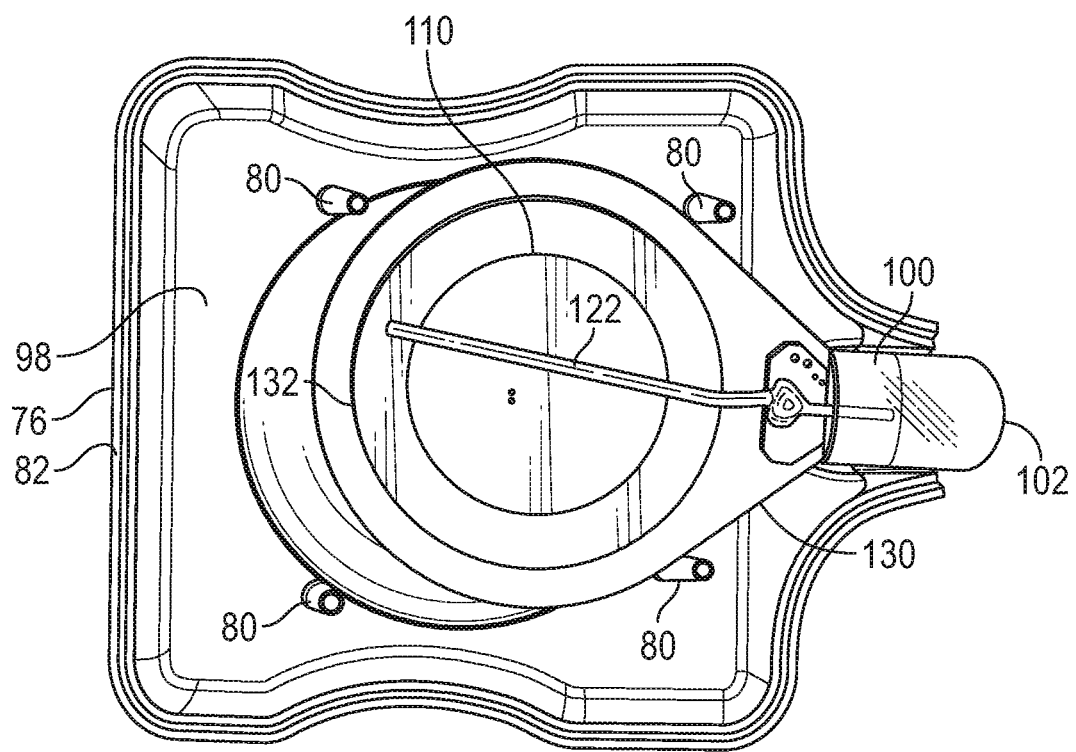
FIG. 12 is a top plan view of components of the exemplary sterile light system of FIG. 1.

As shown in FIGS. 8, 9, and 12, the sterile light assembly 24 may further comprise one or more power source 110 connected to the light emitting diode 100. In one embodiment, the power source 110 may be one or more battery. In one embodiment, the power source 110 may be one or more three-volt battery.

Figure 13:
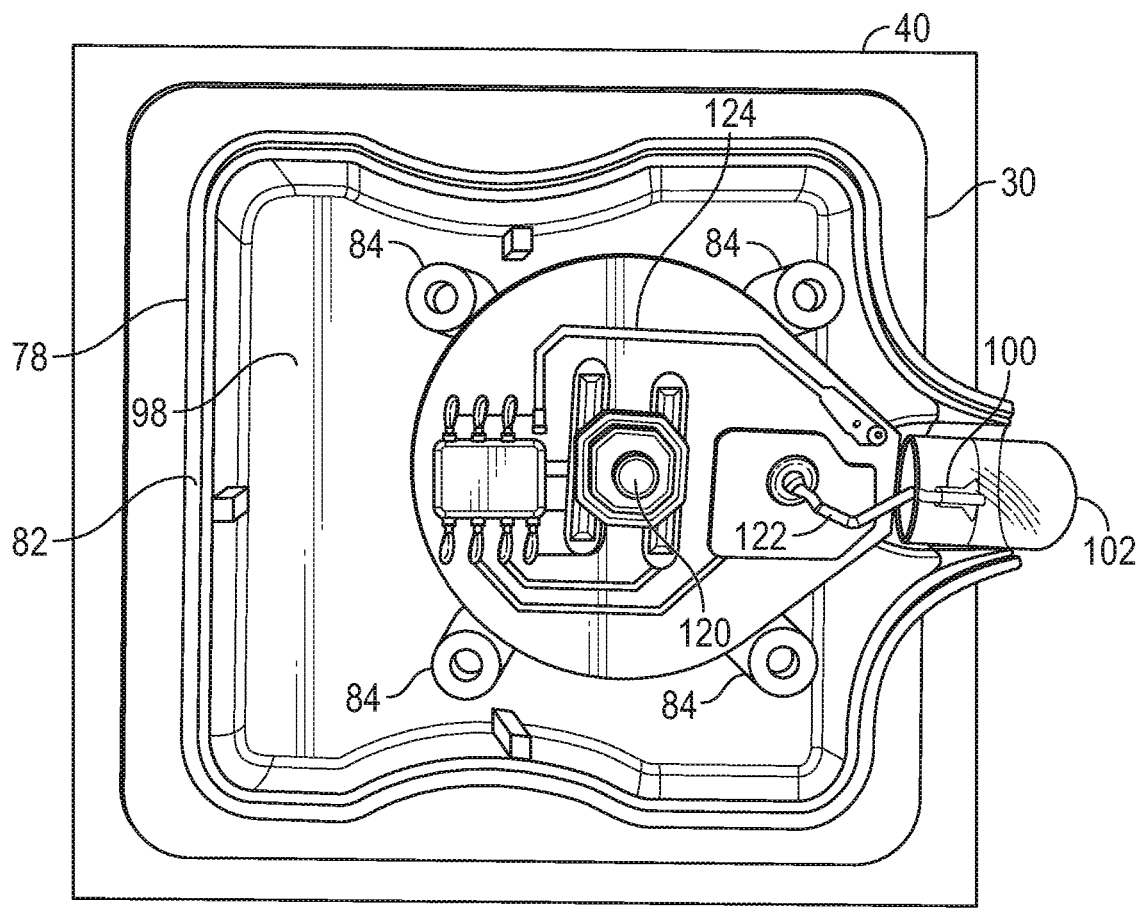
FIG. 13 is a top plan view of components of the exemplary sterile light system of FIG. 1.
Figure 14:
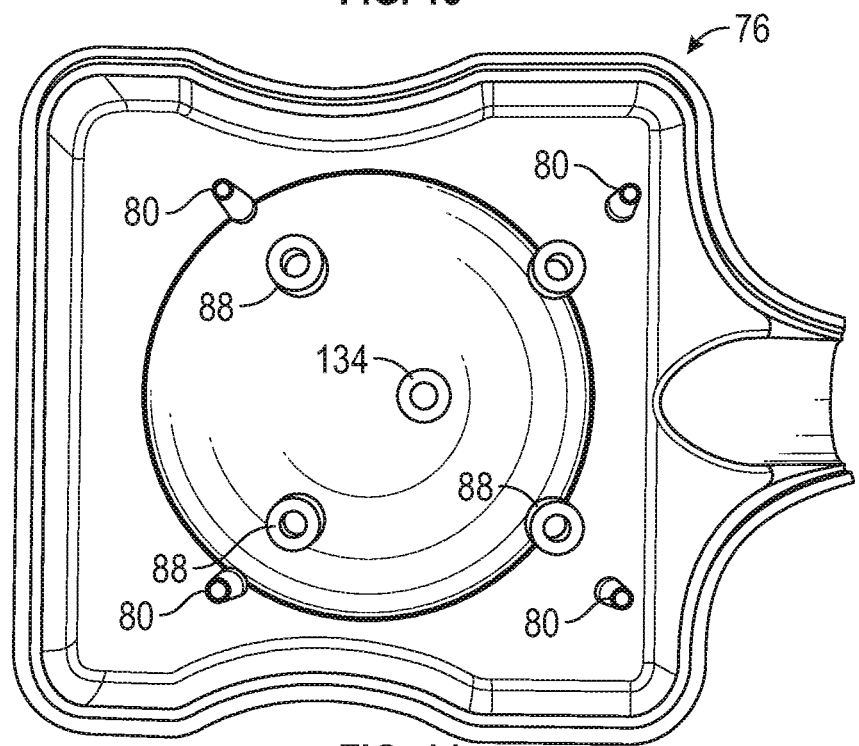
FIG. 14 is a top plan view of components of the exemplary sterile light system of FIG. 1.
Figure 15:
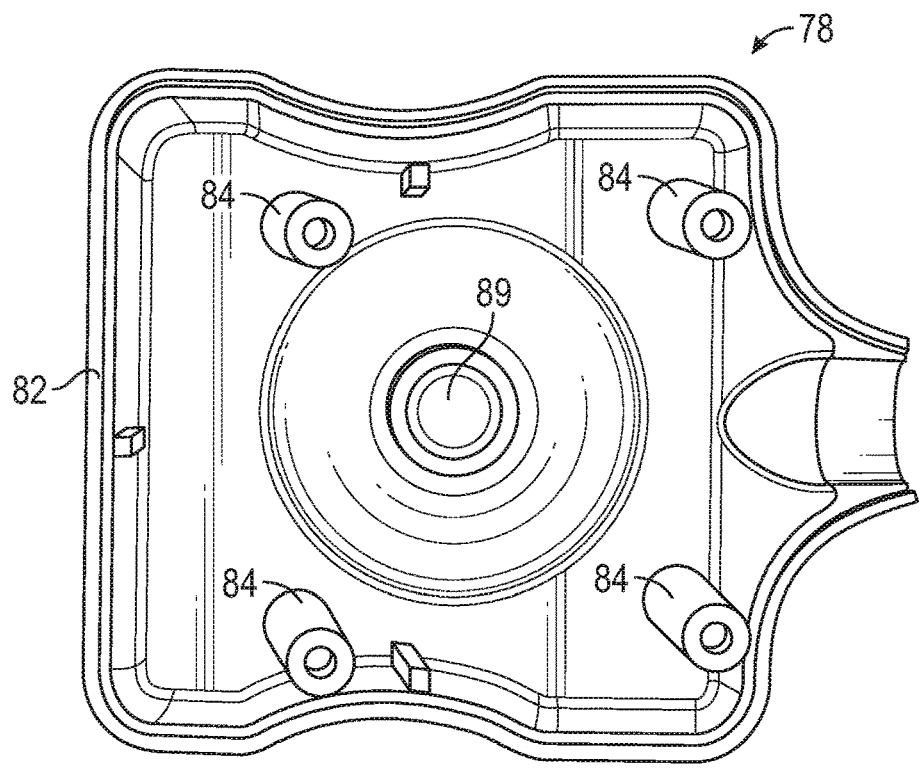
FIG. 15 is a top plan view of components of the exemplary sterile light system of FIG. 1.

As shown in FIGS. 8, 9, and 13, the sterile light assembly 24 may further comprise one or more switch 120 connected to the light emitting diode 100 and the power source 110 such that the switch 120 controls a flow of power from the power source 110 to the light emitting diode 100. In one embodiment, the light emitting diode 100, the power source 110, and the switch 120 are connected via one or more leads 122.

In one embodiment, the light assembly 24 may further comprise a control board 130 connected to and/or supporting the light emitting diode 100, the power source 110, and the switch 120. The control board 130 may be configured and/or programmed and/or programmable to control the light emitting diode 100, the power source 110, and/or the switch 120. In one embodiment, the light emitting diode 100, the power source 110, and the switch 120 are connected via one or more leads 122 and/or traces 124. In one embodiment, the control board 130 may comprise one or more contact pad 132 in contact with the power source 110.

In one embodiment, the one or more stops 88 of the top portion 76 and/or the bottom portion 78 are positioned to stop the top portion 76 and/or the bottom portion 78 of the case 60 from being depressed beyond the length of the gap between the stops 88 and one or more of the light emitting diode 100, the power source 110, the switch 120, and the control board 130, in the interior cavity 98 of the case 60. In one embodiment, the one or more supports 89 of the top portion 76 and/or the bottom portion 78 are positioned to support one or more of the light emitting diode 100, the power source 110, the switch 120, and the control board 130. In one embodiment, the one or more supports 89 are positioned to contact the one or more leads 122 and to keep the one or more leads 122 in contact with the power source 110.

In one embodiment, the one or more supports 89, the one or more cylindrical protrusions 84, and/or the one/or more pins 82 may act to position and/or stabilize one or more of the light emitting diode 100, the power source 110, the switch 120, and the control board 130 in relation to the cavity 98 of the case 60.

In one embodiment, the switch 120 is a momentary contact switch and circuit. In one embodiment, the switch 120 is accessible through the case 60.

In one embodiment, the switch 120 may be activated by being depressed to turn on and off the flow of power from the power source 110 to the light emitting diode 100. The switch 120 may be located within the case 60 and the switch 120 may be activated by being depressed by depressing one or more of the first side 72, the second side 74, the front 68, the back 70, the top 64, and the bottom 66 of the case 60.

In one embodiment, the switch is located within the case 60 proximate to the top 64, the first side 72, and/or the second side 74 of the case, and the switch 120 may be toggled (that is, connecting or disconnecting the power source 110 to the light emitting diode 100) by being depressed through depressing one or more of the top 64, the first side 72, and/or the second side 74 of the case 60.

In one embodiment, the switch 120 may be located within the case 60 and the switch 120 may be toggled by being depressed when a user depresses one or more thinned portion 92, depression 94, and/or raised portion 96, of one or more of the first side 72, the second side 74, the front 68, the back 70, the top 64, and the bottom 66 of the case 60. In one embodiment, the case 60 may have one or more protrusion 134 into the cavity 98 of the interior of the case 60 that aligns with the switch 120, and the switch 120 may be activated by being depressed when the protrusion 134 contacts the switch 120 when the user depresses a portion of the case 60.

Figure 17:
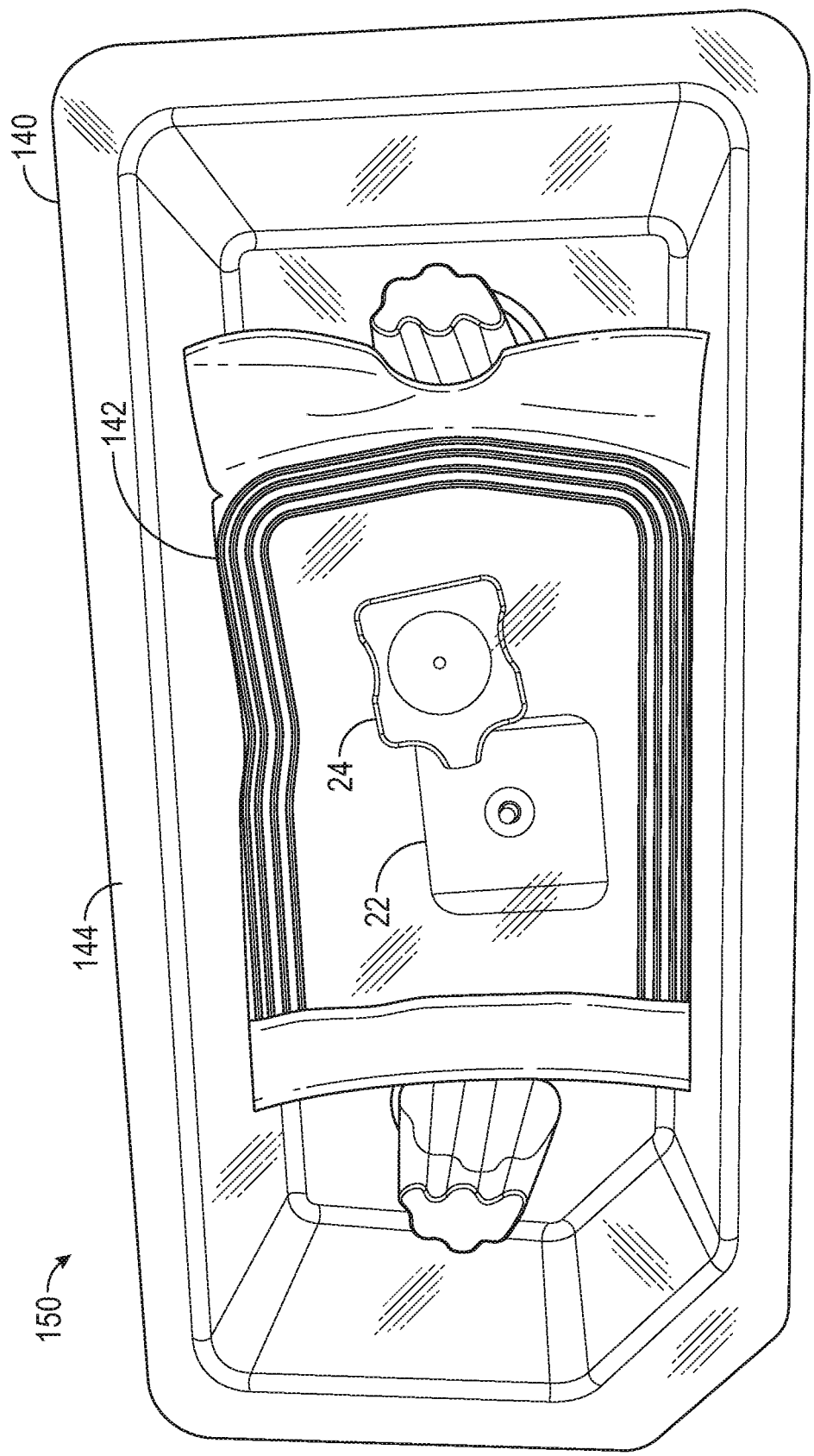
FIG. 17 is a top plan view of a kit in accordance with the present disclosure.

In one embodiment, the sterile light system 20 may be packaged in packaging 140 to maintain sterility of the sterile light system 20. As shown in FIG. 17, the packaging 140 may be structured to protect the sterile light system 20 from contamination and/or damage. In one embodiment, the packaging 140 may include a sealed flexible pouch 142 and/or a substantially rigid clam shell package 144. In one embodiment, the clam shell package 144 may encompass the sealed flexible pouch 142. In one embodiment, the clam shell package 144 may encompass a plurality of sterile light systems 20, each of the plurality of sterile light systems 20 within one of a plurality of the sealed flexible pouch 142.

In one embodiment, the sterile light system 20 may be part of a kit 150. The kit 150 may comprise the sterile light assembly 24 and one or more of the pad assembly 22. In one embodiment, the kit 150 may comprise the sterile light assembly 24 and two of the pad assemblies 22. The kit 150 may comprise packaging 140 encompassing the sterile light assembly 24 and one or more of the pad assembly 22. In one embodiment, the kit 150 may comprise the plurality of sealed flexible pouches 142, each of the plurality of sealed flexible pouches 142 encompassing one of a plurality of the sterile light assembly 24 and one or more of a plurality of the pad assembly 22.

Referring now to FIGS. 1-17, exemplary methods of use of the sterile light system in accordance with the present disclosure will be described. It will be understood that other uses are contemplated and that the following examples are not exclusive of other uses.

In one embodiment, a user, such as medical personnel or caregiver, performs a method for providing hands-free illumination during medical procedures or other care-giving to a patient 42. The patient 42 may be a human or other animal.

The user may obtain the sterile light system 20. The user may remove the packaging 140 to access the sterile light system 20.

In one embodiment, the sterile light system 20 may be pre-assembled with the sterile light assembly 24 already rotatably attached to the sterile pad assembly 22. In another embodiment, the user may rotatably attach the sterile light assembly 24 to the sterile pad assembly 22 by pushing the distal end 52 of the post 32 of the pad assembly 22 into the opening 62 of the case 60 of the sterile light assembly 24.

The user may remove the protective sheet 40 covering the adhesive 38 on the second side 36 of the pad 30, such that the adhesive 38 is exposed. The user may then place the second side 36 of the pad 30 on the patient 42 such that the adhesive 38 contacts the patient 42, such as on the skin of the patient 42.

In one embodiment, the user may test the patient 42 for an allergic reaction to the adhesive 38 by placing the second side 36 of the pad 30 on the patient 42 such that the adhesive 38 contacts the patient 42 for a predetermined time, removing the pad assembly 22, and examining the application site on the patient 42 for signs of contact dermatitis, skin irritation, and/or allergic reaction. The predetermined time may vary. Non-exclusive examples of the predetermined time include thirty seconds, sixty seconds, two minutes, three minutes, four minutes, and five minutes.

In one embodiment, the user may additionally or alternatively place the adhesive 38 of the second side 36 of the pad 30 of the sterile light system 20 of a second sterile light system 20 on the user's body, such as the user's hand, arm, finger, wrist, head, etc., in order to illuminate or further illuminate the desired area of the patient 42.

The user may place the sterile light system 20 on the patient 42 in a location that will allow the sterile light system 20 to illuminate a desired area of the patient 42. The desired area of the patient 42 may be any area that requires care or applied procedures. Nonexclusive examples of such areas include a wound site, a catheter insertion site, a central line insertion site, an intravenous tube insertion cite, a burn site, a surgical site, site of repair of episiotomy and tears at childbirth, and so on.

The user may rotate the light assembly 24 about the distal end 52 of the post 32, adjusting any or all of yaw, pitch, and roll of the light assembly 24, in order to direct the illumination to the desired area of the patient 42.

The user may toggle the switch 120 to activate or deactivate the light emitting diode 100. The user may depress a portion of the case 60, such as a raised portion 92, depression 94, thinned portion 96, top 64, first side 72, and/or second side 74 of the case 60, in order to toggle the switch 120 to activate or deactivate the light emitting diode 100.

Figure 16:
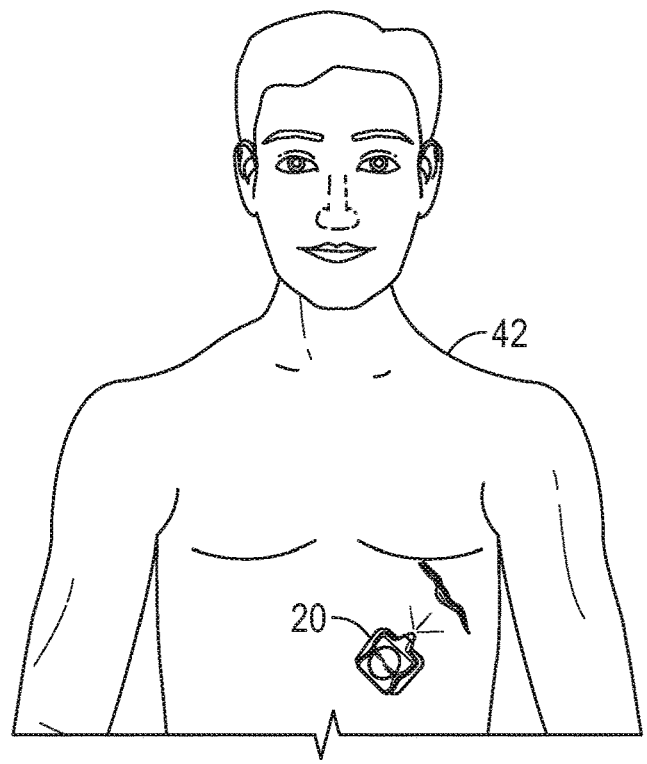
FIG. 16 is a perspective view of an exemplary sterile light system in use in accordance with the present disclosure.

Once the light emitting diode 100 illuminates the desired area of the patient, as illustrated in FIG. 16, the user may perform the medical procedure or care-giving procedure on the patient 42 in the area illuminated by the sterile light system 20. Non-exclusive examples of such procedures include examining, cleaning, debriding, cauterizing, bandaging, and/or stitching a wound site, inserting a catheter in a catheter insertion site, inserting a central line in a central line insertion site, inserting an intravenous tube in a an intravenous tube insertion site, cleaning or debriding a burn site, casting or setting a bone, performing a surgical procedure, performing repair of episiotomy and tears from childbirth, performing an examination, and so on. The sterile light system 20 may be particularly useful for use during procedures on patients having conditions that cause the patient to be visually sensitive to light, non-exclusive examples of which include patients having epilepsy, preeclampsia, or eclampsia.

In one embodiment, the user may remove the sterile light system 20 from the patient 42 by peeling the pad 30 from the patient 42 and then the user may re-apply the pad 30 to another location on the patient 42. In one embodiment, the user may remove the sterile light system 20 from the patient 42 by peeling the pad 30 from the patient 42, remove the sterile light assembly 24 from the pad assembly 22 by detaching the opening 62 of the case 60 from the distal end 52 of the post 32, obtain a new sterile pad assembly 22, rotatably attach the opening 62 of the case 60 to the distal end 52 of the post 32 of the new sterile pad assembly 22, remove the protective sheet 40 from the adhesive 38 of the new sterile pad assembly 22, and attach the sterile light system 20 with the new sterile pad assembly 22 to the patient 42 by placing the adhesive 38 on the second side of the pad 30 against the skin of the patient 42.

Once the medical procedure is complete, the user may deactivate the light emitting diode 100 by toggling the switch 120, such as by depressing the switch 120, and shutting off power from the power source 110. The user may remove the sterile light system 20 from the patient 42 by peeling the pad 30 from the skin of the patient 42. In one embodiment, the user may apply a quantity of water to the area on the patient 42 to dissolve the adhesive 38 to assist in removal of the sterile light system 20. It will be understood that the user may deactivate the light emitting diode 100 before or after removing the sterile light system 20 from the patient 42.

The user may dispose of the sterile light system 20 in accordance with safe medical equipment disposal procedures. In one embodiment, the user may remove the sterile light assembly 24 from the pad assembly 22, dispose of the pad assembly 22 in accordance with safe medical equipment disposal procedures, and re-use the sterile light assembly 24. In one embodiment, the user may, or may cause to, sterilize the sterile light assembly 24 for re-use.

CONCLUSION

Conventionally, overhead lights, ambient lights, or lights worn by those providing care have been used to illuminate an area of a patient 42 for medical care. However, the previously known methods and systems have been insufficient to provide adequate, non-intrusive, and steady illumination to a desired area on a patient in order to perform medical procedures or care-giving procedures. In accordance with the present disclosure, systems and methods are disclosed that provide hands-free illumination of a desired area of a patient during medical procedures and care-giving procedures.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A light system, comprising:
   a pad assembly comprising:
      a pad having a first side and a second side opposite the first side, the first side having an adhesive thereon;
      a removable protective sheet covering the adhesive such that the adhesive is exposed when the protective sheet is removed; and
      a post with a proximal end connected to the second side of the pad and extending to a rounded distal end; and
   a light assembly attachable to and rotatable about the rounded distal end of the post of the pad assembly, the light assembly comprising:
      a case having an opening, the opening structured to rotatably accept the rounded distal end of the post of the pad assembly;
      one or more light emitting diode at least partially within the case and positioned to illuminate an area outside of the case;
      one or more power source connected to the light emitting diode; and
      one or more switch accessible through the case and connected to the light emitting diode and the power source such that the switch controls a flow of power from the power source to the light emitting diode.

2. The light system of claim 1, wherein the opening structured to rotatably accept the rounded distal end of the post of the pad assembly is structured to accept the rounded distal end of the post such that pitch, roll, and yaw of the light assembly on the post are adjustable.

3. The light system of claim 2, wherein the opening structured to rotatably accept the rounded distal end of the post of the pad assembly is structured to maintain an adjusted position of the light assembly.

4. The light system of claim 1, wherein the pad assembly is an electrocardiography pad and electrode.

5. The light system of claim 1, wherein the case further has a top, a bottom, a front, a back, a first side extending from the front to the back between the top and the bottom, and a second side opposite the first side and extending from the front to the back between the top and the bottom, and in which the opening structured to rotatably accept the rounded distal end is located on the bottom of the case.

6. The light system of claim 5, wherein the switch is located within the case and is structured to be activated to turn on the flow of power from the power source to the light emitting diode by depressing one or more of the top, the first side, the second side, the back, and the front of the case.

7. The light system of claim 5, wherein one or more of the first side, the second side, the front, and the back of the case is ergonomically shaped to accept fingers of a user of the light system.

8. The light system of claim 5, wherein the light emitting diode is proximate to the front of the case.

9. The light system of claim 5, wherein the switch is located within the case proximate to the top of the case and is structured to be activated to turn on the flow of power from the power source by depressing the top of the case.

10. The light system of claim 1, wherein one or both of the light assembly and the pad assembly are sterile.

11. The light system of claim 1, wherein the rounded distal end of the post has a larger diameter than a center portion of the post.

12. The light system of claim 11, wherein the rounded distal end of the post has a first diameter, and the opening of the case is a rounded opening having a second diameter smaller than the first diameter, such that attaching the light assembly to the rounded distal end of the post of the pad assembly creates a press fit between the opening and the post.

13. The light system of claim 1, wherein the light assembly snaps onto the pad assembly.

14. The light system of claim 1, wherein the light assembly further comprises a control board connected to the light emitting diode, the switch, and the power source.

15. The light system of claim 1, wherein the case of the light assembly comprises a top portion attached to a bottom portion.

16. The light system of claim 1, wherein the opening of the case of the light assembly is structured to engage and disengage the rounded distal end of the post of the pad assembly.

17. The light assembly of claim 16, wherein the rounded distal end of the post has a first diameter, and the opening of the case is rounded and has a second diameter smaller than the first diameter of the rounded distal end of the post.

18. A light system kit, comprising:
   two or more pad assemblies, each comprising:
      a pad having a first side and a second side opposite the first side, the first side having an adhesive thereon;
      a removable protective sheet covering the adhesive such that the adhesive is exposed when the protective sheet is removed; and
      a post with a proximal end connected to the second side of the pad and extending to a rounded distal end; and
   a light assembly attachable to and rotatable about the rounded distal end of the posts of the pad assemblies, the light assembly comprising:
      a case having an opening, the opening structured to rotatably accept the rounded distal end of the posts of the pad assemblies;
      one or more light emitting diode at least partially within the case and positioned to illuminate an area outside of the case;
      one or more power source connected to the light emitting diode; and
      one or more switch accessible through the case and connected to the light emitting diode and the power source such that the switch controls a flow of power from the power source to the light emitting diode;
   wherein the light assembly is exchangeable between the two or more pad assemblies.

19. The light system kit of claim 18, wherein the opening of the case of the light assembly structured to rotatably accept the rounded distal end of the posts of the pad assemblies is structured to accept the rounded distal end of the posts such that pitch, roll, and yaw of the light assembly on the post are adjustable.

20. The light system kit of claim 19, wherein the opening structured to rotatably accept the rounded distal end of the posts of the pad assemblies is structured to maintain an adjusted position of the light assembly.

* * * * *